United States Patent [19]
Jarman et al.

[11] Patent Number: 5,983,122
[45] Date of Patent: Nov. 9, 1999

[54] APPARATUS AND METHOD FOR IMPROVED PHOTOPLETHYSMOGRAPHIC MONITORING OF MULTIPLE HEMOGLOBIN SPECIES USING EMITTERS HAVING OPTIMIZED CENTER WAVELENGTHS

[75] Inventors: Kristin H. Jarman, Lafayette; Jonas A. Pologe, Boulder, both of Colo.

[73] Assignee: Ohmeda Inc., Louisville, Colo.

[21] Appl. No.: 08/989,528

[22] Filed: Dec. 12, 1997

[51] Int. Cl.⁶ ................................................... A61B 5/00
[52] U.S. Cl. ............................................. 600/323; 356/41
[58] Field of Search .................................. 600/310, 322, 600/323, 328, 473, 476; 356/39, 40, 41

[56] References Cited

U.S. PATENT DOCUMENTS

| | | | |
|---|---|---|---|
| 5,413,100 | 5/1995 | Barthelemy et al. | |
| 5,692,503 | 12/1997 | Kuestner | 600/322 |
| 5,720,284 | 2/1998 | Aoyagi et al. | 600/323 |

FOREIGN PATENT DOCUMENTS

WO 97/47233  12/1997  WIPO.

OTHER PUBLICATIONS

Prof. J. Schwider/University Erlangen–Nürmberg.—Ger, amu. 1995/1996.

*Primary Examiner*—Cary E. O'Connor
*Assistant Examiner*—Eric F. Winakur
*Attorney, Agent, or Firm*—Holme Roberts & Owen LLP

[57] ABSTRACT

An improved method and apparatus for the photoplethysmographic monitoring of blood analyte parameters, specifically oxyhemoglobin, deoxyhemoglobin (reduced hemoglobin), carboxyhemoglobin and, in addition, in a four emitter apparatus, methemoglobin, uses a plurality of beams of light having different spectral contents to trans-illuminate the tissue of a patient. The apparatus and method require the application of an emitter set comprised of four emitters. The emitters may be LED's or laser diodes. In the three analyte system the center wavelength of the emitters must fall within three specific bands. In the four emitter system (capable of measuring methemoglobin) the center wavelength of the emitters in the emitter set must fall within four predetermined bands and the emitters having the two lowest center wavelengths must be at least 5 nanometers apart. The apparatus can use emitters which are located either in a probe, or, preferably, in the monitor, as well as a photodiode which can either be located in the patient probe or in the monitor.

24 Claims, 4 Drawing Sheets

APPARATUS AND METHOD FOR IMPROVED PHOTOPLETHYSMOGRAPHIC MONITORING OF MULTIPLE HEMOGLOBIN SPECIES USING EMITTERS HAVING OPTIMIZED CENTER WAVELENGTHS

BACKGROUND OF THE INVENTION

The present invention generally concerns the monitoring of a patient's tissue using a photoplethysmographic device to generate information related to the concentration of oxyhemoglobin (O2Hb), deoxyhemoglobin or reduced hemoglobin (RHb), carboxyhemoglobin (COHb) and, additionally, methemoglobin (MetHb) in the patient's blood. More specifically, the application relates to a device for the measurement of such blood analytes using a set of emitters having optimal spectral contents defined by a set of specific wavelength ranges.

During emergency evaluation, surgery and other medical procedures, clinicians often want to know the oxygen concentration of the blood, as well as other factors. In pulse oximetry the relative concentration of oxyhemoglobin and deoxyhemoglobin is displayed as a percentage of total hemoglobin in order to provide data on the oxygenation of the patient's blood. Blood oxygenation can be adversely affected by the generation of additional hemoglobin species, called dyshemoglobins. Most notably, carboxyhemoglobin is generated when carbon monoxide molecules bind to the hemoglobin in blood. An accurate measurement of carboxyhemoglobin concentration in the patient's blood may be needed when the patient is a smoker or if carbon monoxide poisoning is suspected. Additionally, elevated methemoglobin levels in the blood can be caused by various medications, illegal drugs and certain pathological conditions such as sickle cell anemia. Therefore measurement of the methemoglobin concentration is also useful during patient evaluation.

Pulse-oximeters have been commercially available for measuring the oxygen saturation, or percent oxyhemoglobin, in arterial blood. These instruments rely on time-varying absorption of light by tissue supplied with pulsating arterial blood with a technique known generally as photoplethysmography. Conventional pulse oximeter instruments transmit light having spectral contents defined by two different center wavelengths through tissue.

The basic physical property that allows the measurement of arterial oxygen saturation by pulse oximetry is that the blood changes color with saturation. A pulse oximeter measures the "color" of the arterial blood and correlates this "color" to a given oxygen saturation to be displayed. When blood is well oxygenated it does not absorb a great deal of red light but as it desaturates it absorbs more and more red light giving the blood a darker appearance. The opposite behavior occurs in the near infrared region (from about 810 nanometers to 1000 nanometers) where hemoglobin absorbs more light when saturated with oxygen than when desaturated. For this reason current pulse oximeters use two emitters, usually light emitting diodes (LED's), one generating light in the red region, having a spectral content usually centered around 660 nanometers, and one generating light in the near infrared region having a spectral content usually centered around 925 or 940 nanometers.

The most obvious limitation of pulse oximetry derives from the fact that it is only a two channel (two wavelength bands) system and therefore can only solve for two components in the blood. Pulse oximetry makes the assumption that only oxyhemoglobin and reduced hemoglobin are present in the arterial blood. Any additional chromophores that are present in arterial blood and which absorb light in the wavelength bands used by the instrument will lead to erroneous readings. Two such chromophores are carboxyhemoglobin and methemoglobin. In particular, if carboxyhemoglobin or methemoglobin is present in above normal levels, a conventional pulse oximeter will give falsely high readings for the arterial oxygen saturation. This is one of the most serious and potentially dangerous limitations of current pulse oximetry.

Prior art pulse oximeters have so far lacked a means to compensate for errors in the measurement of oxyhemoglobin and reduced hemoglobin due to the presence of carboxyhemoglobin and methemoglobin in the blood. The manufacture of non-invasive devices which measure the concentration of various blood analytes such as oxyhemoglobin, deoxyhemoglobin, carboxyhemoglobin and methemoglobin has been attempted by others. However, there has been no successful low-cost commercial implementation of a photoplethysmographic monitor which is capable of accurately measuring all four blood analytes. The present invention overcomes this deficiency by providing a novel method and apparatus for generating accurate concentration estimates for either three or four blood analytes: oxyhemoglobin, reduced hemoglobin, carboxyhemoglobin and, in the four analyte embodiment, methemoglobin.

U.S. Pat. No. 5,413,100 to Barthelemy et al. (the "Barthelemy patent") describes a photoplethysmographic device for measuring oxyhemoglobin, reduced hemoglobin, and carboxyhemoglobin using three laser diode emitters having spectral contents characterized by the center wavelengths of 660 nm, 750 nm and 940 nm. By using an emitter having a spectral content characterized by a center wavelength of 660 nm as the lowest of the three spectral contents, a photoplethysmographic monitor designed according to Barthelemy et al. cannot accurately measure carboxyhemoglobin. No commercially acceptable photoplethysmographic device for the measurement of oxyhemoglobin, carboxyhemoglobin and deoxyhemoglobin has been developed based on the use of light detected from emitters having spectral contents as defined in the Barthelemy patent.

BRIEF SUMMARY OF THE INVENTION

This application discloses a photoplethysmographic apparatus and method for the accurate continuous, real-time, noninvasive measurement of a plurality of blood analyte concentrations, particularly the concentrations (as a percent of total hemoglobin) of the oxyhemoglobin, deoxyhemoglobin, carboxyhemoglobin and, in additional embodiments, methemoglobin levels in blood. The apparatus uses three emitters for measuring oxyhemoglobin, deoxyhemoglobin and carboxyhemoglobin or four emitters for measuring methemoglobin in addition to the former three analytes. Each of the emitters has a spectral content characterized by a wavelength that falls within a wavelength range which has been determined to be the optimal wavelength range for measuring the set of three or four blood analytes.

The method of the invention is the optimization of the specific centerwavelengths necessary for accurate measurement of the oxyhemoglobin, deoxyhemoglobin, carboxyhemoglobin and additionally methemoglobin.

A photoplethysmographic method according to the present invention comprises the step of generating at least three monochromatic or essentially monochromatic beams of light having at least distinct first, second and third spectral contents denoted by center wavelengths $\lambda_1$, $\lambda_2$ and $\lambda_3$. The terms "monochromatic beams of light" or "essentially monochromatic beams of light" are used to refer to light generated by emitters such as a laser diode or other relatively narrow band source, or light of narrow spectral bandwidth, isolated by the use of gratings or interference filters, originating from a broadband source such as a tungsten lamp. A fourth emitter having a spectral content characterized by center wavelength $\lambda_4$ is used in systems where methemoglobin levels are desired.

The light from the emitters is then directed into a portion of the tissue of the patient in order to pass light through the tissue portion along an optical path. The method of the invention further comprises the use of means for detecting the received light transmitted from the tissue such as a photodiode or other appropriate detector. $I_{\lambda 1}$, $I_{\lambda 2}$ and $I_{\lambda 3}$ (and $I_{\lambda 4}$ in the four emitter apparatus) are the measurements of the light received from tissue after absorption and modulation by the various absorbers in the tissue and arterial blood under test.

From the received light measurements, $I_{\lambda 1}$, $I_{\lambda 2}$, and $I_{\lambda 3}$ (and $I_{\lambda 4}$ in the four emitter case), the differential absorptions (dA's) of the transmitted light by various absorbers in the blood are calculated. These differential absorptions (dA's) are then used in the estimation of the blood analyte levels according to known techniques described or referenced herein.

In the present invention, the emitters are chosen so that the spectral contents (denoted by center wavelengths $\lambda_1$, $\lambda_2$ and $\lambda_3$ for the three emitter apparatus and $\lambda_1$, $\lambda_2$ $\lambda_3$ and $\lambda_4$ for the four emitter apparatus) are optimized for the detection of the oxyhemoglobin, deoxyhemoglobin, carboxyhemoglobin and, additionally, in the four emitter case, methemoglobin. The center wavelength for the first, second and third emitters in the three emitter apparatus should be in the range of approximately 610–640 nm, 680–770 nm and 850–1000 nm. The center wavelength for the fourth emitter, in the four emitter apparatus should be in the range of 635–650 nm with the additional constraint that the center wavelength of the first emitter must be at least 5 nm less than the center wavelength of the fourth emitter.

BRIEF DESCRIPTION OF THE DRAWINGS

Preferred embodiments of the invention are described below with reference to the following drawings.

DETAILED DESCRIPTION OF THE INVENTION

The photoplethysmographic monitor of the present invention measures the concentration of oxyhemoglobin (O2Hb), deoxyhemoglobin or reduced hemoglobin (RHb), carboxyhemoglobin (COHb) and, if four emitter are used, methemoglobin (MetHb) in a patient's blood. This is accomplished through the use of at least three emitters (or a filtered broadband emitter) emitting beams of light having a spectral content characterized by center wavelengths, $\lambda_1$ $\lambda_2$, and $\lambda_3$ (and $\lambda_4$ in the four emitter case). The spectral content of the light emitted by the three or four emitters (or filtered broadband emitter) must be distinct and it is preferable that the center wavelengths for each of the emitters also be distinct so that $\lambda_1 \neq \lambda_2 \neq \lambda_3 \neq \lambda_4$.

Figure 1:
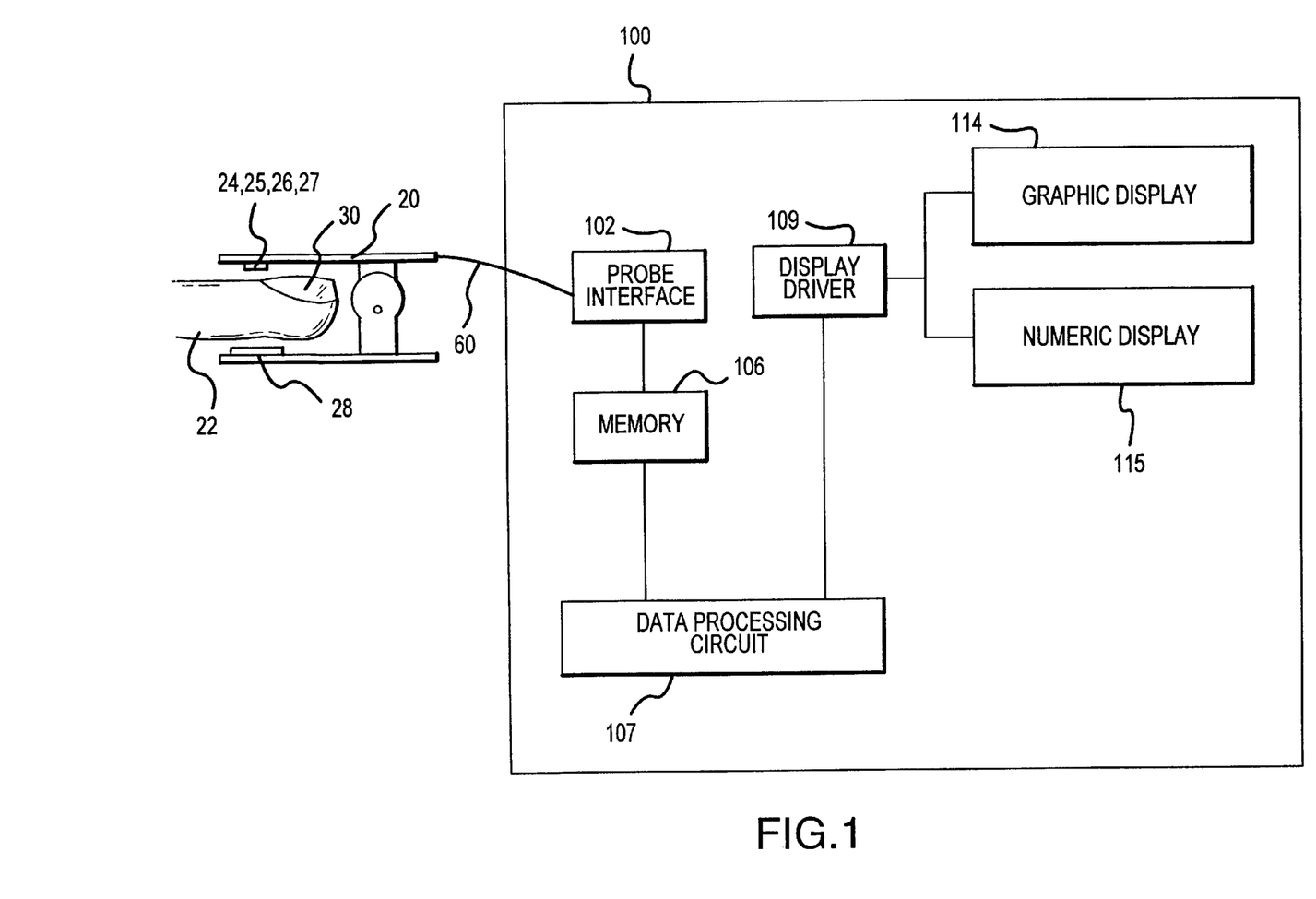
FIG. 1 is a diagram showing an embodiment of the apparatus of the claimed invention having four emitters.

FIG. 1 depicts an apparatus having four emitters made according to the present invention. The three emitter apparatus would be essentially identical except for the lack of one emitter and corresponding channel. Probe 20 is placed on the tissue under test 22 so that a plurality of emitters 24, 25, 26, 27 transmit light through the tissue which is then received by one or more photodetectors 28. Emitters 24, 25, 26, 27 (or a filtered broadband light source) each emit light having a distinct spectral content characterized by a distinct center wavelength denoted by $\lambda_1$ $\lambda_2$, $\lambda_3$ and $\lambda_4$. In the case of a finger probe, the emitters are arranged to emit the light at or near the base of the fingernail 30. These emitters may be light-emitting-diodes (LED's) or laser diodes. It is also possible to filter a broadband light source to produce light having four spectral peaks of differing wavelengths. However, the preferred embodiment is to use at least four separate emitters preferably laser diodes each producing light with a distinct spectral content. It should be understood that four emitters could be used to measure three blood analytes, such as carboxyhemoglobin, oxyhemoglobin and deoxyhemoglobin or methemoglobin, oxyhemoglobin and deoxyhemoglobin. Additionally, a number of emitters greater than the number of blood analytes being measured may be used in a photoplethysmographic system in order to create an overdetermined system. Through cable 60, an electrical signal indicative of the light emitted by emitters 24, 25, 26 and 27, transmitted through finger 22 and received by photodetector 28 is transmitted back to monitor 100. The internal components of monitor 100 are described in detail below.

Figure 2:
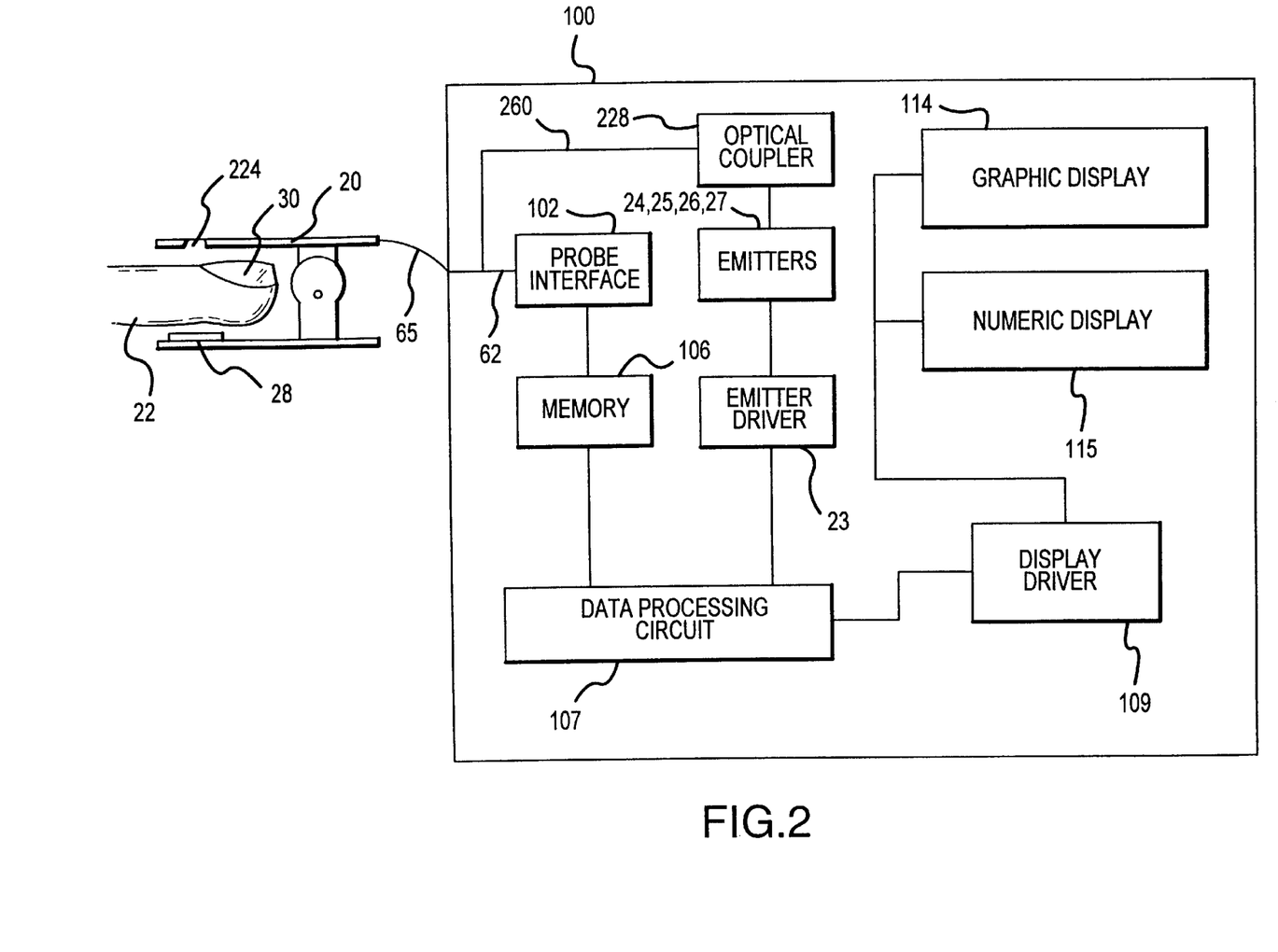
FIG. 2 is a diagram showing a preferred embodiment of the apparatus of the claimed invention.

A preferred method of implementing the apparatus of the present invention is depicted in FIG. 2. The emitters 24, 25, 26 and 27 (which may be LED's or laser diodes, but which are preferably laser diodes) are housed in the monitor 100. The emitters 24, 25, 26 and 27 are driven by emitter driver 23 which is controlled by the data processing circuit 107. The emitted light is then combined by an optical coupler 228 and transmitted to the probe 20 by optical fiber 260 or other such optically transmissive material residing in electro-optical cable 65. The light transmitted to the finger 22 by optical fiber 260 and electro-optical cable 65 passes through window or opening 224 in probe 20 and thereby illuminates the finger at the base of fingernail 30. Transmitted light is received by photodetector 28 which sends an electrical signal back through the electro-optical cable 65 to the probe interface 102 and on to data processing circuit 107 in monitor 100. The transmission of the emitted light can be controlled in a time division multiplexing manner and an optical coupler 228 can be used to provide a means for combining multiple emitters onto one strand of optical fiber 260.

In a photoplethysmographic system of the present invention, the intensity of light transmitted through the tissue under test is measured by one or more photodetectors 28 which provide a signal corresponding to the intensity of light received denoted $I_{\lambda 1}$, $I_{\lambda 2}$, $I_{\lambda 3}$ and $I_{\lambda 4}$. In the monitor the analog received intensity signals, $I_{\lambda 1}$, $I_{\lambda 2}$, $I_{\lambda 3}$ and $I_{\lambda 4}$, are converted into digital equivalents through an analog to digital (A/D) converter which is part of probe interface 102. The intensity signals are then stored in memory 106 and manipulated in data processing circuit 107 of the monitor 100 according to data processing instructions stored in memory 106 and executed by the data processing circuit 107 in order to determine an estimate of the blood analyte concentrations. Blood analyte concentrations may then be displayed via display driver 109 and graphic display 114 and/or numeric display 115.

Figure 3:
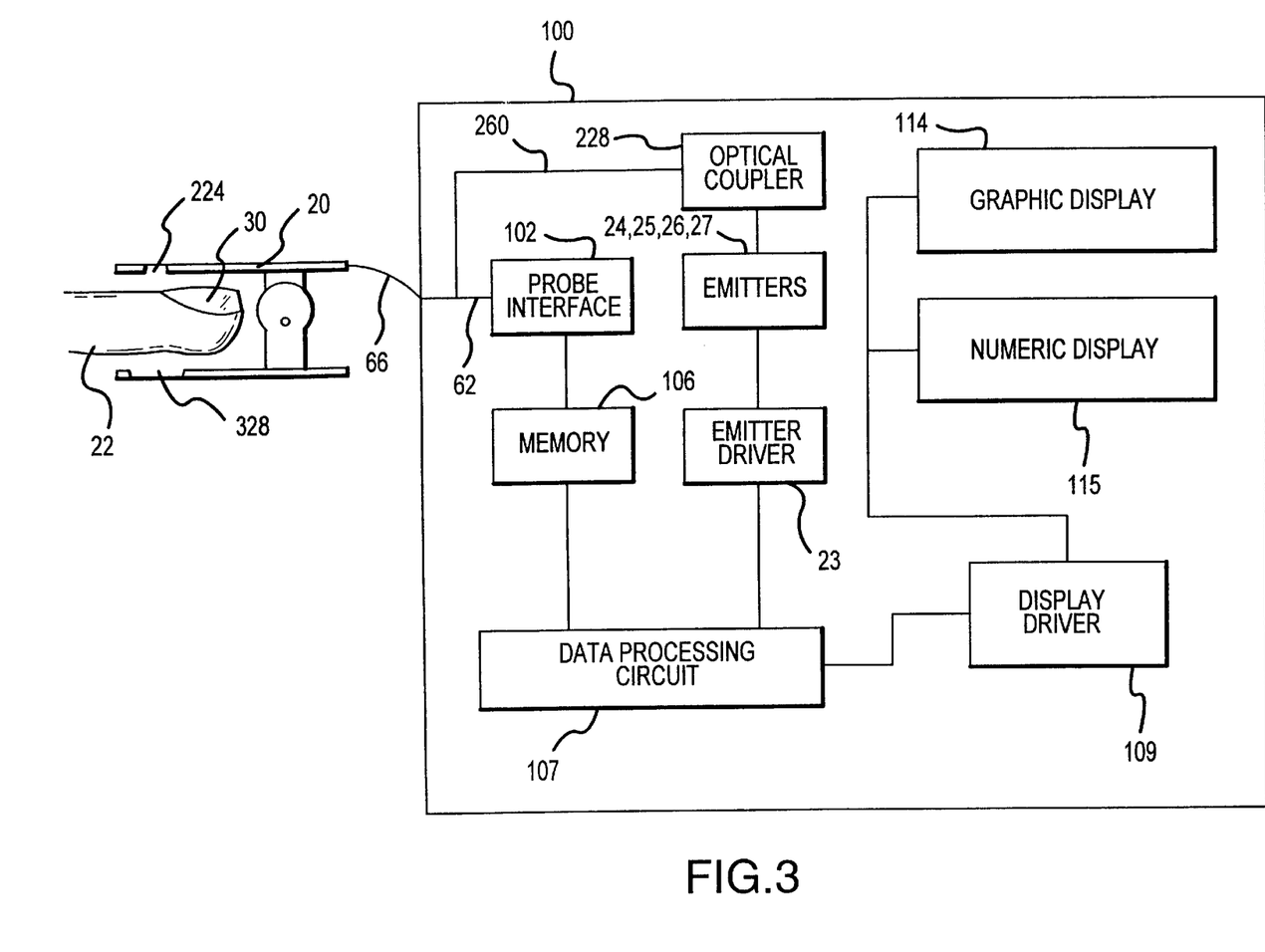
FIG. 3 is a diagram showing an additional embodiment of the claimed invention.

FIG. 3 depicts an additional embodiment of the present invention in which the photodiode is located in the monitor 100 as part of probe interface 102 rather than in the probe 20. Light is transmitted from the probe 20 via an optical fiber in optical cable 66. The light is then transmitted through window or opening 224 into finger 22. Light is then received through window or opening 328 onto another optical fiber internally disposed within probe 20 which then forms part of optical cable 66. In this embodiment there is no need for electrical current to be transmitted to the probe 20, thus the probe may be useful in applications where electrical conductors are undesirable such as in magnetic resonance imaging. All other elements of FIG. 3 work in appreciably the same manner as the other embodiments described above.

For each distinct spectral content employed by the system as characterized by the center wavelengths $\lambda = \lambda_1, \lambda_2, \lambda_3$ and $\lambda_4$, the differential absorption, $dA_\lambda$ of the light for any two adjacent samples is calculated according to the following formula, for example for $\lambda_1$:

$$dA_{\lambda 1} \approx \Delta A_{\lambda 1} = \frac{[I_{\lambda 1}(t_j) - I_{\lambda 1}(t_{j-1})]}{[I_{\lambda 1}(t_j) + I_{\lambda 1}(t_{j-1})]/2} \tag{1}$$

where $I_{\lambda 1}*t_j)$ is the intensity at time $t_j$ and $I_{\lambda 1}(t_{j-1})$ is the intensity of the previous sample time.

The differential absorption at wavelength $\lambda$ is also approximately equal to:

$$\Delta A_{\lambda} = E_\lambda^O C^O \Delta L^O + E_\lambda^R C^R \Delta L^R + E_\lambda^{CO} C^{CO} \Delta L^{CO} + E_\lambda^{Met} C^{Met} \Delta L^{Met} \tag{2}$$

Where C is the concentration of the specific absorber, E is the extinction for that absorber at wavelength $\lambda$ and $\Delta L$ is the differential change in effective path length the transmitted light has traveled. (Superscripts O, R, CO, and Met refer to O2Hb, RHb, COHb, and MetHb respectively.) Thus, after measuring the received light intensities and knowing the extinction coefficient E for each wavelength it is possible to determine the concentrations of the specific absorbers. In the three emitter system the same calculations are made according to the following equation:

$$\Delta A_\lambda = E_\lambda^O C^O \Delta L^O + E_\lambda^R C^R \Delta L^R + E_\lambda^{CO} C^{CO} \Delta L^{CO} \tag{3}$$

In the present invention, normalized differential absorptions are used to obtain the analyte concentration values. From the differential absorptions, $dA_{\lambda 1}$, $dA_{\lambda 2}$, $dA_{\lambda 3}$ and $dA_{\lambda 4}$, normalized differential absorptions are computed by taking the ratio of differential absorptions at two different center wavelengths. For example, for center wavelengths $\lambda_2$ and $\lambda_1$, the normalized dA is computed as $$N_{21} = dA_{\lambda 2}/dA_{\lambda 1}. \tag{4}$$

These normalized differential absorptions (normalized dA's) may be computed in a number of different ways. In particular, instead of simply taking a ratio, the normalized dA may also be computed as the slope of the regression line obtained from least squares regression by regressing $dA_{\lambda 2}$ on $dA_{\lambda 1}$. As one skilled in the art will understand such alternative methods for computing the normalized differential absorptions such as that described in U.S. Pat. No. 5,503,148 are hereby incorporated by reference.

The normalized dA's are then used in a calibration equation to obtain the measured analyte values. In one embodiment of the present invention, the calibration equation is given by $$xHb = \frac{a_1 + a_2 N_{21} + a_3 N_{31} + a_4 N_{41}}{b_1 + b_2 N_{21} + b_3 N_{31} + b_4 N_{41}} \tag{5}$$

where xHb refers to one of $O_2Hb$, RHb, COHb, or MetHb, the constants $a_1$, $a_2$, $a_3$, $a_4$, $b_1$, $b_2$, $b_3$, and $b_4$ are calibration coefficients determined previously in a calibration experiment, and $N_{21}$, $N_{31}$, and $N_{41}$ are normalized dAs for channels 2 and 1, 3 and 1, and 4 and 1, respectively. As one skilled in the art will understand, however, the calibration equation for each analyte is not limited to this form of equation, and may be, for example, a polynomial.

In the three emitter system the calibration equation is given by:

$$xHb = \frac{a_1 + a_2 N_{21} + a_3 N_{31}}{b_1 + b_2 N_{21} + b_3 N_{31}} \tag{6}$$

where xHb refers to one of $O_2Hb$, RHb or COHb, the constants $a_1$, $a_2$, $a_3$, $b_1$, $b_2$, and $b_3$ are calibration coefficients determined previously in a calibration experiments, and $N_{21}$ and $N_{31}$ are normalized dAs for channels 2 and 1 and 3 and 1, respectively.

Figure 4:
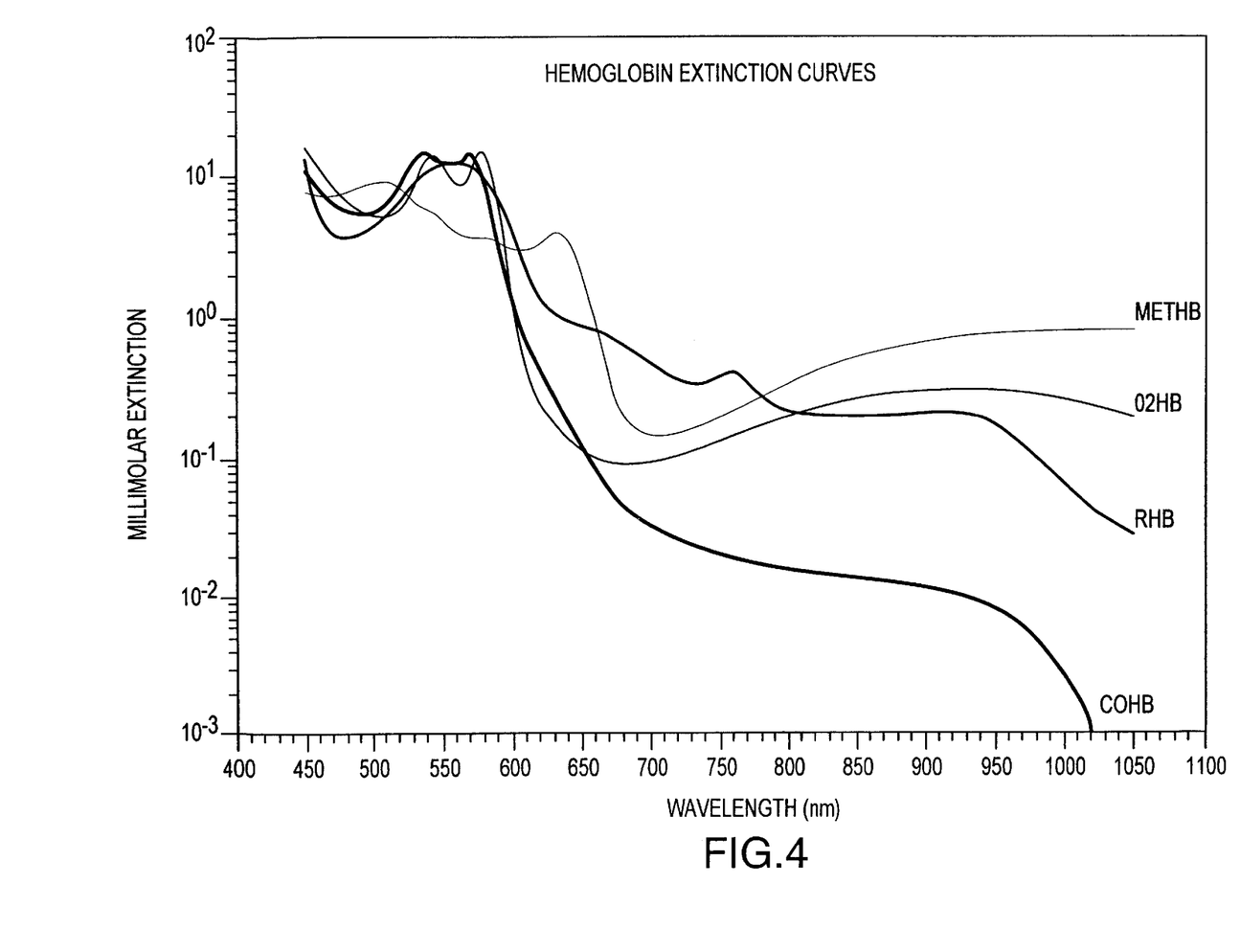
FIG. 4 is a graph of the extinction curves of oxyhemoglobin, reduced hemoglobin, carboxyhemoglobin and methemoglobin in terms of millimolar extinction, on a logarithmic scale, versus wavelength in nanometers.

The present invention improves over all prior art methods which have attempted to provide apparatus and methods for the measurement of blood analytes other than reduced hemoglobin (Rim) and oxygenated hemoglobin ($O_2Hb$). FIG. 4 is a graph of the extinction curves of oxyhemoglobin, reduced hemoglobin, carboxyhemoglobin and methemoglobin in terms of millimolar extinction, on a logarithmic scale, versus wavelength in nanometers. The spectral contents of the emitters selected by Barthelemy for the measurement of COHb, RHb and $O_2Hb$ concentrations had center wavelengths at 660, 750 and 940 nm. As can be seen from FIG. 4, the extinction curve for carboxyhemoglobin is low and is rapidly dropping in the range of 600 nm to 1000 nm. In general, a low extinction value for a particular hemoglobin species at a given wavelength means that very little light is absorbed by that species, (i.e., the hemoglobin species is virtually transparent to that wavelength of light). As a result, the amount of light absorbed will not change with the amount of that particular species present, thereby making measurement of that species very difficult at the given wavelength. In Barthelemy the lowest center wavelength is 660 nm where the millimolar extinction of carboxyhemoglobin is already quite low.

Therefore, in the three emitter embodiment of the present invention, the first emitter of the set should be characterized by a center wavelength in the range of 610–640 nm. This emitter provides carboxyhemoglobin extinction values that are roughly three times the extinction values at 660 nm so that carboxyhemoglobin can be measured much more accurately. The second emitter should have a spectral content characterized by a center wavelength in the range of 680–770 nm and the third emitter should have a spectral content characterized by a center wavelength between 850–1000 nm.

Data from a system according to this design is set forth in the second half of Table 1 below, along with the accuracy obtained. The first half of Table 1 shows the accuracy of the three wavelength system described in Barthelemy. As can be seen, unacceptably inaccurate results are obtained if the optimized three wavelength system disclosed herein is not use. MAE refers to the mean absolute error and SDPD refers to the root mean squared error of prediction.

TABLE 1

| EMITTER SET | MEASURE OF ERROR | Oxy-hemoglobin | Deoxy-hemoglobin | Carboxy-hemoglobin |
|---|---|---|---|---|
| 660, 750, 905 | MAE | 4.47 | 4.51 | 3.00 |
| | SDPD | 5.61 | 6.02 | 4.66 |
| | max(error) | 14.77 | 15.23 | 11.73 |
| 632, 750 905 | MAE | 1.63 | 1.22 | 2.26 |
| | SDPD | 2.24 | 1.49 | 2.69 |
| | max(error) | 5.24 | 3.50 | 4.79 |

TABLE 1

The four emitter embodiment of the apparatus allows for the measurement of methemoglobin in addition to the other three blood analytes measured by the three emitter system. The use of four emitters diminishes interference by the presence of methemoglobin on the measurement of the other three blood analytes of concern, i.e., COHb, RHb, and $O_2Hb$. A three emitter system would not be sufficiently accurate in the measurement of the latter three blood analytes if any significant amount of MetHb were present. The fourth emitter should have a spectral content characterized by a center wavelength in the range of 635–650 nm.

In addition, the center wavelength characterizing the spectral content of the fourth emitter must be at least 5 nm greater than the center wavelength characterizing the spectral content of the first emitter, i.e., $\lambda_4 > \lambda_1 + 5$ nm. This constraint on the selection of these two emitters with the lowest center wavelengths ensures sufficiently distinct spectral contents so as to obtain unique information about all analytes from each emitter.

Table 2 set forth below provides empirical data supporting the selection of emitters having center wavelengths in the ranges discussed above and with the 5 nm difference constraint between the emitters with the shortest wavelengths. The results are for in vitro calibration for $O_2Hb$, RHb and COHb.

TABLE 2

| EMITTER SET | MEASURE OF ERROR | Oxyhemoglobin | Carboxyhemoglobin |
|---|---|---|---|
| 660, 750, 940 | MAE | 4.47 | 3.00 |
| | SDPD | 5.61 | 4.66 |
| | max(error) | 14.77 | 11.73 |
| 632, 640, 750, 905 | MAE | 1.63 | 1.19 |
| | SDPD | 2.24 | 1.67 |
| | max(error) | 5.24 | 3.84 |

TABLE 2

As can be seen from the data in Table 2, the use of the four emitters 632, 640, 750 and 905 provides a significant improvement in the measurement of $O_2Hb$ and COHb in comparison to the wavelengths used by Barthelemy, i.e., 660, 759 and 940.

The prior art disclosure of Barthelemy is a three emitter system. The following Table 3 also shows the improvement of using four emitters in the preferred range in comparison to a number of other four emitter sets outside of the preferred range. The measurements of all four blood analytes were taken in an in vitro calibration study. The two sets in bold typeface are in the preferred range.

TABLE 3

| EMITTER SET | MEASURE OF ERROR | Oxy-hemo-globin | Reduced hemo-globin | Carboxy-hemo-globin | Met-hemo-globin |
|---|---|---|---|---|---|
| 632, 640 750, 905 | MAE | 1.63 | 0.60 | 1.19 | 1.45 |
| | SDPD | 2.24 | 0.79 | 1.67 | 1.91 |
| | max(error) | 5.24 | 1.77 | 3.84 | 4.72 |
| 632, 640 670, 905 | MAE | 5.65 | 4.20 | 2.47 | 1.76 |
| | SDPD | 6.36 | 5.64 | 3.66 | 2.39 |
| | max(error) | 10.56 | 13.70 | 8.70 | 5.21 |
| 632, 640 690, 905 | MAE | 1.71 | 1.08 | 1.94 | 0.51 |
| | SDPD | 2.40 | 1.22 | 2.87 | 0.72 |
| | max(error) | 5.52 | 1.86 | 6.24 | 1.55 |
| 632, 640 810, 905 | MAE | 2.74 | 1.20 | 2.69 | 3.12 |
| | SDPD | 3.45 | 1.64 | 3.40 | 3.74 |
| | max(error) | 6.85 | 3.75 | 6.57 | 5.90 |
| 632, 655 750, 905 | MAE | 1.35 | 1.08 | 2.15 | 1.44 |
| | SDPD | 1.78 | 1.98 | 3.39 | 2.42 |
| | max(error) | 3.70 | 6.42 | 8.59 | 7.62 |
| 632, 670 750, 905 | MAE | 1.89 | 1.15 | 2.74 | 2.62 |
| | SDPD | 2.29 | 1.76 | 3.85 | 4.11 |
| | max(error) | 4.62 | 5.34 | 7.91 | 12.13 |

TABLE 3

Thus, using emitter sets comprising four emitters having spectral contents characterized by a center wavelength within the four wavelength ranges (610–640 nm, 635–650 nm, 680–770 nm and 850–1000 nm) and subject to the one difference constraint, i.e., that the two lowest center wavelengths be 5 nanometers apart, provides an improved photoplethysmographic system for the measurement of oxyhemoglobin, reduced hemoglobin, carboxyhemoglobin and methemoglobin.

The measurement of blood analytes by light non-invasively is also limited by the "tissue-window." The tissue window extends from nearly 600 nm out to a little beyond 1100 nm. At wavelengths shorter than the tissue window the blood is so opaque that very little light can pass through as is evident from the hemoglobin extinction curves in FIG. 4. At wavelengths above the tissue window water begins to increase in opacity and again makes it difficult to pass safe light levels through the tissue. Therefore, one important aspect of this invention is the use of at least one wavelength shorter than the isobestic point for reduced hemoglobin and carboxyhemoglobin, i.e., shorter than 650 nm. Selecting one or more wavelengths below 650 nm guarantees us an extinction for carboxyhemoglobin that is of great enough magnitude to enhance the accuracy of measurement of carboxyhemoglobin. Therefore, the critical teaching of this invention is the use of a light wavelength between 600 nm and 650 nm where carboxyhemoglobin has sufficiently high extinction to be easily measured but not so high as to virtually extinguish the incident light.

In FIG. 4, the steepness of the extinction curves for oxyhemoglobin and carboxyhemoglobin in the 600 nm to 650 nm region graphically shows the need for stable and monochromatic or essentially monochromatic light in this region such as that provided by laser diodes.

While various embodiments of the present invention have been described in detail, it is apparent that modifications and adaptations of those embodiments will occur to those skilled in the art. For example, it should be appreciated that the method and apparatus as taught by the present invention may be modified in an unlimited number of ways within the framework of the teachings of the present invention.

Additionally, other characteristics such as centroid, peak wavelength, etc. may be used to characterize the spectral content of the light emitted by the emitters. These variations are all considered to fall within the scope of the present invention. Therefore, it is to be expressly understood that such modifications and adaptations are within the spirit and scope of the present invention, as set forth in the following claims.

We claim:

1. An apparatus for the measurement of a concentration value for a plurality of blood analytes comprising:
    a set of emitters which illuminate the tissue portion of the patient with a plurality of light signals each having a distinct spectral content characterized by a center wavelength wherein the center wavelength characterizing a first emitter is between approximately 610 and 640 nm, the center wavelength characterizing a second emitter is between approximately 680 and 770 nm, the center wavelength characterizing a third emitter is between approximately 850 and 1000 nm,
    a photodetector which detects the light transmitted through the tissue portion and generates a plurality of received light intensity signals;
    a central processing unit;
    a means for communicating said plurality of received light intensity signals from the photodetector to said central processing unit;
    wherein said central processing unit calculates the concentration value for each of the plurality of blood analytes from the plurality of received light intensity signals.

2. The apparatus of claim 1 wherein the plurality of blood analytes comprises oxyhemoglobin, dexoyhemoglobin and carboxyhemoglobin.

3. The apparatus of claim 2 wherein the center wavelength characterizing said first emitter is approximately 632 nm.

4. The apparatus of claim 3 wherein the center wavelength characterizing said second emitter is 750 nm and the center wavelength characterizing said third emitter is 905 nm.

5. The apparatus of claim 1 further comprising a fourth emitter having a spectral content characterized by a center wavelength between approximately 635 and 650 nm and wherein the fourth emitter is at least 5 nm greater than said first emitter.

6. The apparatus of claim 5 wherein the plurality of blood analytes comprises oxyhemoglobin, dexoyhemoglobin, carboxyhemoglobin and methemoglobin.

7. The apparatus of claim 6 wherein the center wavelength characterizing said first emitter is approximately 632 nm and the center wavelength characterizing the fourth emitter is approximately 640 nm.

8. The apparatus of claim 1 wherein the means for communicating said plurality of received light intensity signals from the photodetector to said central processing unit comprises an electrical conductor.

9. An apparatus for the measurement of a concentration value for each of a plurality of blood analytes of a tissue of a patient comprising a monitor and a probe: said monitor comprising;
    an emitter block located in said monitor in communication with said tissue through one or more optical fibers wherein said emitter block comprises:
        a first emitter having a spectral content characterized by a center wavelength between approximately 610 and 640 nm;
        a second emitter having a spectral content characterized by a center wavelength between approximately 680 and 770 nm;
        a third emitter having a spectral content characterized by a center wavelength between approximately 850 and 1000 nm;
    a probe interface connected with said probe for receiving signals indicative of the light transmitted through said tissue; and,
    a processing unit for generating said concentration values from said received light signals; and,
    said probe comprising:
        an optical fiber for transmitting the light emitted from the first, second and third emitters to said tissue;
        a means for generating received light signals indicative of the absorption of light by the plurality of blood analytes in said tissue; and,
        a means for transmitting said received light signals to said probe interface.

10. The apparatus of claim 9 wherein the center wavelength characterizing said first emitter is approximately 632 nm.

11. The apparatus of claim 9 wherein the center wavelength characterizing said first emitter is approximately 632 nm, the center wavelength characterizing said second emitter is 750 nm and the center wavelength characterizing said third emitter is 905 nm.

12. The apparatus of claim 9 wherein the blood analytes comprise oxyhemoglobin, deoxyhemoglobin and carboxyhemoglobin.

13. The apparatus of claim 12 wherein the plurality of blood analytes further comprises methemoglobin and the emitter block further comprises a fourth emitter having a spectral content characterized by a center wavelength between approximately 635 and 650 nm.

14. The apparatus of claim 13 wherein the center wavelength of the fourth emitter is at least 5 nm greater the center wavelength of the first emitter.

15. The apparatus of claim 14 wherein the received light signals are electrical, the means for generating the received light signals is a photoconductor and the means for transmitting said received light signals to said probe interface comprises an electrical conductor.

16. The apparatus of claim 14 wherein the received light signals are optical, the means for generating the received light signal is an optically transmissive window and the means for transmitting said received light signals to said probe interface comprises an optical fiber.

17. The apparatus of claim 9 wherein the received light signals are electrical, the means for generating the received light signals is a photoconductor and the means for transmitting said received light signals to said probe interface comprises an electrical conductor.

18. The apparatus of claim 9 wherein the received light signals are optical, the means for generating the received light signal is an optically transmissive window and the means for transmitting said received light signals to said probe interface comprises an optical fiber.

19. A method for determining a concentration value for oxyhemoglobin, deoxyhemoglobin and carboxyhemoglobin in a tissue of a patient comprising the steps of:
    illuminating the tissue with a first emitter having a spectral content characterized by a center wavelength between approximately 610 and 640 nm;
    illuminating the tissue with a second emitter having a spectral content characterized by a center wavelength between approximately 680 and 770 nm;
    illuminating the tissue with a third emitter having a spectral content characterized by a center wavelength between approximately 850 and 1000 nm;

receiving light transmitted through the tissue to generate a received light intensity signals for each emitter;

generating a concentration value oxyhemoglobin, deoxyhemoglobin and carboxyhemoglobin based on the received light intensity signals.

20. The method according to claim 19 wherein the center wavelength characterizing said first emitter is approximately 632 nm, the center wavelength characterizing said second emitter is approximately 690 nm and the center wavelength characterizing said third emitter is approximately 905 nm.

21. A method for determining a concentration value for a plurality of blood analytes of a tissue of a patient comprising the steps of:

illuminating the tissue with a first emitter having a spectral content characterized by a center wavelength between approximately 610 and 640 nm;

illuminating the tissue with a second emitter having a spectral content characterized by a center wavelength between approximately 635 and 650 nm wherein the center wavelength of said second emitter is at least 5 nm greater than the center wavelength of said first emitter;

illuminating the tissue with a third emitter having a spectral content characterized by a center wavelength between approximately 680 and 770 nm;

illuminating the tissue with a fourth emitter having a spectral content characterized by a center wavelength between approximately 850 and 1000 nm; receiving light transmitted through the tissue to generate a received light intensity signals for each emitter;

generating a concentration value for each of the plurality of blood analytes based on the received light intensity signals.

22. The method according to claim 21 wherein the center wavelength characterizing said first emitter is approximately 632 nm and the center wavelength characterizing said second emitter is between 638 nm and 642 nm.

23. The method according to claim 21 wherein the center wavelength characterizing said first emitter is approximately 632 nm, the center wavelength characterizing said second emitter is approximately 640 nm, the center wavelength characterizing said third emitter is approximately 690 nm and the center wavelength characterizing said fourth emitter is approximately 905 nm.

24. The method according to claim 21 wherein the plurality of blood analytes comprises oxyhemoglobin, deoxyhemoglobin, carboxyhemoglobin and methemoglobin.

* * * * *